US010436687B2

(12) United States Patent
Lui et al.

(10) Patent No.: US 10,436,687 B2
(45) Date of Patent: Oct. 8, 2019

(54) TRANSFER VESSEL AND METHODS FOR REDUCING SAMPLE LOSS

(71) Applicant: Theranos, Inc., Newark, CA (US)

(72) Inventors: Clarissa Lui, Menlo Park, CA (US); Priyanshu Gupta, Hornsby (AU)

(73) Assignee: Theranos IP Company, LLC, New York, NY (US)

( * ) Notice: Subject to any disclaimer, the term of this patent is extended or adjusted under 35 U.S.C. 154(b) by 62 days.

(21) Appl. No.: 15/887,855

(22) Filed: Feb. 2, 2018

(65) Prior Publication Data
US 2018/0224361 A1 Aug. 9, 2018

Related U.S. Application Data

(63) Continuation of application No. PCT/US2016/045199, filed on Aug. 2, 2016.
(Continued)

(51) Int. Cl.
G01N 1/00 (2006.01)
G01N 1/40 (2006.01)
(Continued)

(52) U.S. Cl.
CPC .......... G01N 1/4077 (2013.01); B01L 3/5021 (2013.01); B01L 3/5023 (2013.01); G01N 33/491 (2013.01); B01L 2200/025 (2013.01); B01L 2200/06 (2013.01); B01L 2200/0642 (2013.01); B01L 2200/10 (2013.01); B01L 2300/047 (2013.01); B01L 2300/069 (2013.01);
(Continued)

(58) Field of Classification Search
CPC .......... B01L 2200/025; B01L 2200/06; B01L 2200/0642; B01L 2200/10; B01L 2300/047; B01L 2300/0609; B01L 2300/069; B01L 2300/0858; B01L 2300/0867; B01L 2400/0409; B01L 3/5021; B01L 3/5023; G01N 1/4077; G01N 2001/4083; G01N 33/491
See application file for complete search history.

(56) References Cited

U.S. PATENT DOCUMENTS 3,852,194 A    12/1974   Zine
5,275,731 A *  1/1994    Jahn ............... G01N 33/491
                                                   210/515
5,976,824 A * 11/1999    Gordon ............. B01J 3/006
                                                   210/321.6

FOREIGN PATENT DOCUMENTS

WO    2005056748 A1    6/2005
WO    2015069911 A1    5/2015

OTHER PUBLICATIONS

The International Search Report and the written opinion for PCT/US16/45199 dated Dec. 15, 2016.

* cited by examiner

Primary Examiner — Jennifer Wecker

(57) ABSTRACT

Devices, systems and methods for holding and transferring small volume fluid samples are disclosed. Holding vessels, including holding vessels having two or more internal compartments for holding small volume fluid samples, are disclosed. Transfer vessels for receiving small volume fluid samples from such holding vessels are disclosed. Transfer vessels for combining small volume fluid samples from such holding vessels are disclosed. Methods for providing small volume fluid samples for analysis with small loss of sample are disclosed. Methods for providing small volume fluid samples for analysis using automated sample analysis devices and systems, with small loss of sample, are disclosed.

7 Claims, 6 Drawing Sheets

Related U.S. Application Data

(60) Provisional application No. 62/200,642, filed on Aug. 4, 2015.

(51) Int. Cl.
*G01N 33/49* (2006.01)
*B01L 3/00* (2006.01)

(52) U.S. Cl.
CPC ............... *B01L 2300/0609* (2013.01); *B01L 2300/0858* (2013.01); *B01L 2300/0867* (2013.01); *B01L 2400/0409* (2013.01); *G01N 2001/4083* (2013.01)

TRANSFER VESSEL AND METHODS FOR REDUCING SAMPLE LOSS

BACKGROUND

Collection and transport of biological samples from subjects are important steps in clinical diagnosis. Maintaining the integrity of a biological sample during collection and transport is often critical for obtaining valid clinical results. Where small volumes of sample are obtained, reducing loss of sample may also be a critical factor in obtaining valid clinical results.

However, current methods of obtaining, transporting, maintaining integrity, and utilizing small volume samples may be inadequate to reduce degradation, reduce sample loss, and to provide valid clinical results.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicant discloses herein devices, systems, and methods useful for one or more of obtaining, collecting, combining, and analyzing small volume fluid samples. Small volume fluid samples suitable for use with the devices, systems, and methods disclosed herein include small volume blood samples; for example, devices, systems, and methods disclosed herein provide advantages in the collection, transport, and analysis of fingerstick blood samples and other small volume fluid samples.

In one embodiment, Applicant discloses vessels for receiving biological samples, termed herein "transfer vessels". In embodiments, transfer vessels may be useful for receiving biological samples from sample collection vessels, from sample transport vessels, or other vessels. In embodiments, transfer vessels may be useful for combining biological samples from sample collection vessels, from sample transport vessels, or other vessels. In embodiments, transfer vessels may be useful for receiving portions, or fractions, of biological samples from sample collection vessels, from sample transport vessels, or other vessels. In embodiments, transfer vessels may be useful for combining portions, or fractions, of biological samples from sample collection vessels, from sample transport vessels, or other vessels.

In many instances, the entire sample, or a portion of the sample, must be removed from a collection or transport vessel and transferred to another vessel in order to analyze the sample. Applicant has identified sample loss upon such transfer as a critical limiting factor in obtaining sufficient sample for analysis. Transfer vessels as disclosed herein are suitable for receiving fluid samples from sample collection and sample transport vessels, to combine fluid samples effective to reduce loss of sample during analysis.

Applicant discloses herein transfer vessels suitable for receiving a sample from a sample collection vessel, or from a sample transport vessel, or from another vessel containing a fluid sample. In embodiments, transfer vessels suitable for receiving samples as disclosed herein are configured to receive sample from two or more sample collection vessels, or two or more sample transport vessels, or a sample collection vessel and a sample transport vessel, or from other vessels containing a fluid sample, or combinations thereof. In embodiments, Applicant discloses herein transfer vessels suitable for combining samples from two or more sample collection vessels, or two or more sample transport vessels, or a sample collection vessel and a sample transport vessel, or from other vessels containing a fluid sample, or combinations thereof.

Transfer vessels suitable for these, and other uses, include a cavity and include an upper lip. An upper lip of a transfer vessel having features as disclosed herein may include a bevel. In embodiments, a bevel of an upper lip of a transfer vessel may include an inner bevel; a bevel of an upper lip of a transfer vessel may include an outer bevel; a bevel of an upper lip of a transfer vessel may include a bevel portion extending from the lip in a direction distal to the vessel cavity; and may include combinations thereof. In embodiments, a bevel may extend for the entire perimeter of a lip of a transfer vessel having features as disclosed herein. In embodiments, a bevel may extend for only a portion of the perimeter of a lip of a transfer vessel having features as disclosed herein. In embodiments, a lip of a transfer vessel having features as disclosed herein may include two or more bevels; in embodiments, each of the two or more bevels may extend for only a portion of the perimeter of the lip of a transfer vessel.

In embodiments, a lip of a transfer vessel having features as disclosed herein may include a tab, or a notch, or other feature suitable for guiding the placement of a sample collection vessel, or a sample transport vessel, or other vessel, for positioning for transfer of the contents of the sample collection vessel, or a sample transport vessel, or other vessel, into the transfer vessel. In embodiments, such a tab, or notch, or other feature may extend outwardly from the lip of the transfer vessel away from the cavity of the transfer vessel. In embodiments, such a tab, or notch, or other feature may extend inwardly from the lip of the transfer vessel into or towards the cavity of the transfer vessel. In embodiments, a transfer vessel having features as disclosed herein may include combinations of some or all of such lip, bevel, tab, notch, and other features disclosed herein.

In embodiments, a transfer vessel having features as disclosed herein may include a shoulder, or catch, or other feature configured to rest on a support. In embodiments, such a shoulder, or catch, or other feature may extend outwardly from the transfer vessel away from the cavity of the transfer vessel. In embodiments, such a shoulder, or catch, or other feature may extend outwardly from the lip of the transfer vessel away from the cavity of the transfer vessel. In embodiments, such a shoulder, or catch, or other feature may be configured to be held, or captured, by a transport mechanism, effective to control the placement of the transfer vessel, or effective to move the transfer vessel from one location to another location. In embodiments, such movement of the transfer vessel from one location to another location may comprise movement within an automated sample analysis device, e.g., within the housing of an automated sample analysis device. In embodiments, such movement may be suitable to allow the transfer of a fluid sample, or portion or fraction thereof, from a sample collection vessel, or a sample transport vessel, or other vessel, to the transfer vessel.

Applicant discloses herein vessels for holding a fluid sample that are configured to provide fluid sample to transfer vessels disclosed herein; such vessels are termed herein "holding vessels". In embodiments, holding vessels as disclosed herein are configured to provide fluid sample to transfer vessels, and may include sample collection vessels, sample transport vessels, and other vessels suitable for holding a fluid sample, or portion of a fluid sample, or fraction of a fluid sample. In embodiments, holding vessels suitable for providing samples to transfer vessels as disclosed herein are configured to provide two or more fluid samples, or two or more portions of a fluid sample, to a single transfer vessel. In embodiments, holding vessels suitable for providing samples to transfer vessels as disclosed herein are configured to provide a fluid sample, or portion of a fluid sample, or fraction of a fluid sample, to a transfer vessel which also receives a fluid sample, or a portion of a fluid sample, or a fraction of a fluid sample, from a different holding vessel, effective that fluid samples, or portions or fractions thereof, are combined in a single transfer vessel. In embodiments, combined in a single transfer vessel includes combining such samples or portions or fractions thereof within a cavity of a single transfer vessel. In embodiments, the entire fluid sample held by a holding vessel may be provided to a transfer vessel. In embodiments, less than the entire fluid sample held by a holding vessel may be provided to a transfer vessel. In embodiments, a portion of a fluid sample held by a holding vessel may be provided to a transfer vessel. In embodiments, a fraction of a fluid sample held by a holding vessel may be provided to a transfer vessel.

Holding vessels suitable for these, and other uses, include a cavity and include an upper lip. An upper lip of a holding vessel having features as disclosed herein may include a bevel. In embodiments, a bevel of an upper lip of a holding vessel may include an inner bevel; a bevel of an upper lip of a holding vessel may include an outer bevel; a bevel of an upper lip of a holding vessel may include a bevel portion extending from the lip in a direction distal to the holding vessel cavity; and may include combinations thereof. In embodiments, a bevel may extend for the entire perimeter of a lip of a holding vessel having features as disclosed herein. In embodiments, a bevel may extend for only a portion of the perimeter of a lip of a holding vessel having features as disclosed herein. In embodiments, a lip of a holding vessel having features as disclosed herein may include two or more bevels; in embodiments, each of the two or more bevels may extend for only a portion of the perimeter of the lip of a holding vessel. In embodiments, a lip of a holding vessel having features as disclosed herein may include a tab, or a notch, or other feature suitable for guiding the placement of the holding vessel for positioning for transfer of the contents of the holding vessel into the transfer vessel. In embodiments, such a tab, or notch, or other feature may extend outwardly from the lip of the holding vessel away from the cavity of the holding vessel. In embodiments, such a tab, or notch, or other feature may extend inwardly from the lip of the holding vessel into or towards the cavity of the holding vessel. In embodiments, a holding vessel having features as disclosed herein may include combinations of some or all of such lip, bevel, tab, notch, and other features disclosed herein.

In embodiments, a holding vessel having features as disclosed herein may include a shoulder, or catch, or other feature configured to rest on a support. In embodiments, such a shoulder, or catch, or other feature may extend outwardly from the holding vessel away from the cavity of the holding vessel. In embodiments, such a shoulder, or catch, or other feature may extend outwardly from the lip of the holding vessel away from the cavity of the holding vessel. In embodiments, such a shoulder, or catch, or other feature may be configured to be held, or captured, by a transport mechanism, effective to control the placement of the holding vessel, or effective to move the holding vessel from one location to another location. In embodiments, such movement of the holding vessel from one location to another location may comprise movement within an automated sample analysis device, e.g., within the housing of an automated sample analysis device. In embodiments, such movement may be suitable to allow the transfer of a fluid sample, or portion or fraction thereof, from a holding vessel to the transfer vessel.

Applicant discloses herein systems including transfer vessels configured for receiving a fluid sample, or portion or fraction thereof, from a sample collection vessel, or from a sample transport vessel, or from another vessel containing a fluid sample. Applicant discloses herein systems including transfer vessels configured for receiving fluid samples, or portions or fractions thereof, from two or more holding vessels; in embodiments, such two or more holding vessels may include a sample collection vessel, or a sample transport vessel, or another vessel containing a fluid sample. Applicant discloses herein systems including holding vessels configured to provide a fluid sample, or a portion or a fraction thereof, to transfer vessels as disclosed herein. Applicant discloses herein systems including holding vessels configured to provide fluid samples, or portions or fractions thereof, in conjunction with one or more other holding vessels, to a transfer vessel, effective that such a transfer vessel holds, and combines, fluid samples, or portions or fractions thereof, from two or more holding vessels.

In embodiments, Applicant discloses herein systems comprising a transfer vessel and a holding vessel. In embodiments, Applicant discloses herein systems comprising a transfer vessel and a plurality of holding vessels; for example, such systems may comprise a transfer vessel and two holding vessels, and may comprise a transfer vessel and three, or more, holding vessels.

In embodiments, Applicant discloses herein systems comprising a transfer vessel, a holding vessel, and an automated sample analysis device. In embodiments, Applicant discloses herein systems comprising a transfer vessel, a holding vessel, and an automated sample analysis system. In embodiments, Applicant discloses herein systems comprising a transfer vessel, an automated sample analysis device, and a plurality of holding vessels; for example, such systems may comprise a transfer vessel and two holding vessels, and may comprise a transfer vessel and three, or more, holding vessels. In embodiments, Applicant discloses herein systems comprising a transfer vessel, an automated sample analysis system, and a plurality of holding vessels; for example, such systems may comprise a transfer vessel and two holding vessels, and may comprise a transfer vessel and three, or more, holding vessels.

In embodiments, combining two, or more, small volume fluid samples in a transfer vessel as disclosed herein is effective to reduce the proportionate amount of sample lost during analysis. In embodiments, combining two, or more, small volume fluid samples in a transfer vessel as disclosed herein is effective to reduce the volume of sample lost during analysis. In embodiments, combining two, or more, small volume fluid samples in a transfer vessel as disclosed herein is effective to reduce the proportionate amount of sample lost during aliquotting of portions of a sample during analysis. In embodiments, combining two, or more, small volume fluid samples in a transfer vessel as disclosed herein is effective to reduce the volume of sample lost during aliquotting of portions of a sample during analysis. In embodiments, combining two, or more, small volume fluid samples in a transfer vessel as disclosed herein is effective to reduce the proportionate amount of sample lost during pipetting of portions of a sample during analysis. In embodiments, combining two, or more, small volume fluid samples in a transfer vessel as disclosed herein is effective to reduce the volume of sample lost during pipetting of portions of a sample during analysis. In embodiments, combining two, or more, small volume fluid samples in a transfer vessel as disclosed herein is effective to reduce the proportionate amount of sample remaining in vessels and unavailable for analysis. In embodiments, combining two, or more, small volume fluid samples in a transfer vessel as disclosed herein is effective to reduce the volume of sample remaining in vessels and unavailable for analysis.

In embodiments, combining two, or more, small volume fluid samples in a transfer vessel as disclosed herein is effective to reduce contamination of a sample with non-sample material during analysis of a sample. In embodiments, combining two, or more, small volume fluid samples in a transfer vessel as disclosed herein is effective to reduce to reduce contamination of a sample with material from a sample collection vessel or from a sample transport vessel during analysis of a sample.

In embodiments, Applicant discloses methods for obtaining small volume fluid samples which reduce the proportionate amount, and methods which reduce the volume, of sample lost during sample analysis. In embodiments, Applicant discloses methods for transferring two or more small volume fluid samples which reduce the proportionate amount, and methods which reduce the volume, of sample lost during sample analysis. In embodiments, Applicant discloses methods for combining two or more small volume fluid samples which reduce the proportionate amount, and methods which reduce the volume, of sample lost during sample analysis. In embodiments, Applicant discloses methods for combining two or more small volume fluid samples which increase the proportionate amount, and methods which increase the volume, of sample available for sample analysis as compared to methods which do not combine the small volume fluid samples in transfer vessels as disclosed herein.

The methods, devices, and systems disclosed herein provide advantages over prior methods, devices, and systems. For example, methods, devices, and systems disclosed herein improve the efficiency of sample collection, reduce lost or wasted sample, and are suitable for use with small volume fluid samples. Such small volume fluid samples include small volume blood samples, including venous blood samples, arterial blood samples, capillary blood samples, fingerstick blood samples, and portions and fractions thereof. Use of methods, devices, and systems disclosed herein with small volume fluid samples reduces the amount of sample that may be unavailable for analysis; for example, use of methods, devices, and systems disclosed herein may reduce the amount of fluid sample left within a sample collection vessel, sample transport vessel, or other holding vessel, as compared with the amount of fluid sample left within previous vessels or left by previous methods.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1A:
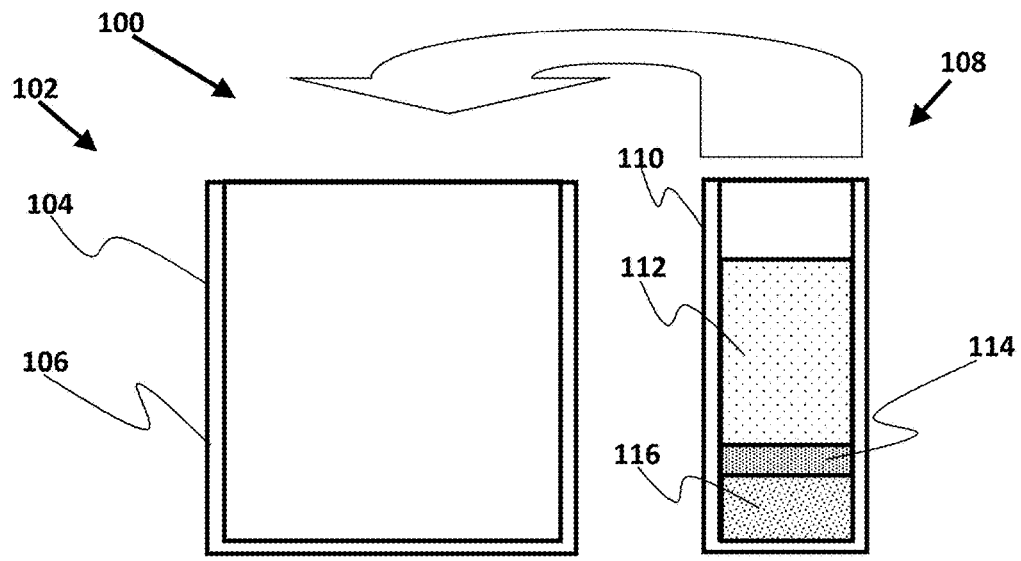
FIG. 1A shows a transfer vessel and a holding vessel, with a fluid sample in the holding vessel. The large arrow indicates the transfer of at least a portion or fraction of the sample from the holding vessel to the transfer vessel.

Description and disclosure of examples of reagents, assays, methods, kits, and exemplary automatic sample analysis devices and systems which may be used with the methods, assays, reagents, devices and systems disclosed herein may be found, for example, in U.S. Pat. No. 7,888,125; in U.S. Pat. Nos. 8,088,593; 8,380,541; 8,435,738; 8,475,739; U.S. patent application Ser. No. 14/712,077, filed May 14, 2015; U.S. patent application Ser. No. 14/481,858, filed Sep. 9, 2014; U.S. patent application Ser. No. 13/769,798, filed Feb. 18, 2013; U.S. patent application Ser. No. 13/769,779, filed Feb. 18, 2013; U.S. patent application Ser. No. 13/769,820, filed Feb. 18, 2013; International Patent Application PCT/US2012/057155, filed Sep. 25, 2012; U.S. application Ser. No. 13/355,458, filed Jan. 20, 2012; International Patent Application PCT/US2011/053189, filed Sep. 25, 2011; U.S. patent application Ser. No. 13/244,946, filed Sep. 26, 2011; U.S. patent application Ser. No. 13/244,949, filed Sep. 26, 2011; and International Patent Application PCT/US2014/016977, filed Feb. 18, 2014, the disclosures of all of which patents and patent applications are hereby incorporated by reference herein in their entireties.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which are defined in the following.

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, a "fraction" of a sample refers to a component of a sample separated or isolated from the complete sample. For example, a sample of blood when obtained from a subject is a sample of whole blood; in embodiments, whole blood may be separated into a plasma fraction (containing the liquid part of blood) and a cellular fraction (containing blood cells; the blood cell fraction may be further fractionated into, for example, white blood cells and red blood cells). In other embodiments, whole blood that is allowed to coagulate, or which is induced to coagulate, may be separated into serum (the liquid portion of blood after coagulation) and the solid, or semi-solid, portion (often termed a "coagulum") resulting from blood coagulation (which includes blood cells and other components such as fibrin (produced by the action of thrombin on fibrinogen)).

As used herein, a "portion" of a sample refers to a part of the entire sample, having the same composition as the entire sample. A portion of a sample is representative of the entire sample, and may be used to analyze the sample for the presence or amount of sample components of interest, since such components are present in the portion in the same relative amounts as in the entire sample.

As used herein, the term "vessel" refers to any container suitable for holding a fluid sample. A vessel may be any container, such as a jar, a tube, a cup, or other container having a cavity which may be accessed for filling the cavity with a fluid, and which may be accessed for removal of the fluid from the cavity. A cavity may be capped with a removable cap or lid, which cap or lid may be moved, or may be removed, to allow access to the cavity.

As used herein, the term "transfer vessel" refers to a vessel for receiving a fluid, typically from another vessel. The acronym "TV" as used herein refers to a transfer vessel. A transfer vessel may receive a fluid sample, such as a biological sample, from another vessel. In embodiments, the other vessel may contain both a biological sample and a gel; upon transferring the biological sample to the transfer vessel, the gel may remain in the other vessel, so that the transfer vessel contains only biological sample after the transfer.

In embodiments, a transfer vessel may receive fluid from two or more other vessels; for example, a transfer vessel may receive fluid from two or more other vessels at the same time. In embodiments, the two or more other vessels may each contain both a biological sample and a gel; upon transferring the biological samples to the transfer vessel, the gel may remain in the other vessels, so that the transfer vessel contains only biological sample after the transfer. Where a transfer from two or more other vessels to a single transfer vessel is performed, the single transfer vessel may then contain a larger volume of biological sample than was contained in each of the two or more other vessels prior to the transfer. Such a transfer from two or more vessels to a single transfer vessel may provide a mixed sample held in the transfer vessel.

As used herein, the term "holding vessel" refers to a vessel for containing a fluid sample. A holding vessel may receive a fluid sample, such as a biological sample, directly from the subject, or may receive the fluid sample from a collection device or another vessel. In embodiments, a holding vessel may contain both a biological sample and a gel; upon transferring the biological sample from such a holding vessel to a transfer vessel, the gel, and a portion or fraction of the sample, may remain in the holding vessel, so that the transfer vessel contains only biological sample after the transfer.

As used herein, the term "bar code" refers to a machine-readable code, typically including stripes that are black and white in color, and may include bars, squares, or other shaped-black and white shapes. A bar code may be typically rectangular in shape, and may be placed on a label, printed on an object, attached to an object, or otherwise associated with an object to be identified.

As used herein, the term "QR code" refers to a machine-readable code, typically including bars, squares, or stripes that are black and white in color, and typically in a square shape, that may be placed on a label, printed on an object, attached to an object, or otherwise associated with an object to be identified.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

A sample collection unit may be used to collect a sample, such as a blood sample from a subject. In embodiments, a sample collection unit comprises a sample collection vessel. In embodiments, a sample collection unit comprises one or more blood collection tubes (e.g., capillary tubes) and a sample collection vessels for holding fingerstick blood obtained by application of the blood collection tubes to blood emerging from a wound in an extremity (e.g., a finger, toe, heel, or other extremity) of a subject.

Automated Sample Analysis Devices and Systems

The devices, systems, and methods disclosed herein may be used in in the analysis of fluid samples on automated sample analysis devices, or on automated sample analysis systems. The assays and methods disclosed herein can be readily incorporated into and used in device for processing a sample, or a system for processing a sample, which may be an automated assay device, or may be an automated assay system. Such an automated sample analysis device, and such an automated sample analysis system, may be used with the devices, including the vessels, disclosed herein, and may be useful for the practice of the methods disclosed herein.

An automated sample analysis device may be part of a system, a component of which may be an automated assay device. A device may be an automated assay device. An automated assay device may be configured to facilitate collection of a sample, prepare a sample for a clinical test, or effect a chemical reaction with one or more reagents or other chemical or physical processing, as disclosed herein. An automated assay device may be configured to obtain data from a sample. An automated assay device may be configured to transmit data obtained from a sample. An automated assay device may be configured to analyze data from a sample. An automated assay device may be configured to communicate with another device, or a laboratory, or an individual affiliated with a laboratory, to analyze data obtained from a sample.

An automated assay device may be configured to be placed in or on a subject. An automated assay device may be configured to accept a sample from a subject, either directly or indirectly. A sample may be, for example, a blood sample (e.g., a sample obtained from a fingerstick, or from venipuncture, or an arterial blood sample), a urine sample, a biopsy sample, a tissue slice, stool sample, or other biological sample; a water sample, a soil sample, a food sample, an air sample; or other sample. A blood sample may comprise, e.g., whole blood, plasma, or serum. An automated assay device may receive a sample from the subject through a housing of the device. The sample collection may occur at a sample collection site, or elsewhere. The sample may be provided to the device at a sample collection site.

In some embodiments, an automated assay device may be configured to accept or hold a cartridge. In some embodiments, an automated assay device may comprise a cartridge. The cartridge may be removable from the automated assay device. In some embodiments, a sample may be provided to the cartridge of the automated assay device. Alternatively, a sample may be provided to another portion of an automated assay device. The cartridge and/or device may comprise a sample collection unit that may be configured to accept a sample.

A cartridge may include a sample, and may include reagents for use in processing or testing a sample, disposables for use in processing or testing a sample, or other materials. Following placement of a cartridge on, or insertion of a cartridge into, an automated assay device, one or more components of the cartridge may be brought into fluid communication with other components of the automated assay device. For example, if a sample is collected at a cartridge, the sample may be transferred to other portions of the automated assay device. Similarly, if one or more reagents are provided on a cartridge, the reagents may be transferred to other portions of the automated assay device, or other components of the automated assay device may be brought to the reagents. In some embodiments, the reagents or components of a cartridge may remain on-board the cartridge. In some embodiments, no fluidics are included that require tubing or that require maintenance (e.g., manual or automated maintenance).

A sample or reagent may be transferred to a device, such as an automated assay device. In embodiments, a sample may be transferred to a device using a vessel, or vessels, as disclosed herein. A sample or reagent may be transferred within a device. Such transfer of sample or reagent may be accomplished without providing a continuous fluid pathway from cartridge to device. Such transfer of sample or reagent may be accomplished without providing a continuous fluid pathway within a device. In embodiments, such transfer of sample or reagent may be accomplished by a sample handling system (e.g., a pipette); for example, a sample, reagent, or aliquot thereof may be aspirated into an open-tipped transfer component, such as a pipette tip, which may be operably connected to a sample handling system which transfers the tip, with the sample, reagent, or aliquot thereof contained within the tip, to a location on or within the automated assay device. The sample, reagent, or aliquot thereof can be deposited at a location on or within the automated assay device. Sample and reagent, or multiple reagents, may be mixed using a sample handling system in a similar manner. One or more components of the cartridge may be transferred in an automated fashion to other portions of the automated assay device, and vice versa.

A device, such as an automated assay device, may have a fluid handling system. A fluid handling system may perform, or may aid in performing, transport, dilution, extraction, aliquotting, mixing, and other actions with a fluid, such as a sample. In some embodiments, a fluid handling system may be contained within a device housing. A fluid handling system may permit the collection, delivery, processing and/or transport of a fluid, dissolution of dry reagents, mixing of liquid and/or dry reagents with a liquid, as well as collection, delivery, processing and/or transport of non-fluidic components, samples, or materials. The fluid may be a sample, a reagent, diluent, wash, dye, or any other fluid that may be used by the device, and may include, but not limited to, homogenous fluids, different liquids, emulsions, suspensions, and other fluids. A fluid handling system, including without limitation a pipette, may also be used to transport vessels (with or without fluid contained therein) around the device. The fluid handling system may dispense or aspirate a fluid. The sample may include one or more particulate or solid matter floating within a fluid.

In embodiments, a fluid handling system may comprise a pipette, pipette tip, syringe, capillary, or other component. The fluid handling system may have portion with an interior surface and an exterior surface and an open end. The fluid handling system may comprise a pipette, which may include a pipette body and a pipette nozzle, and may comprise a pipette tip. A pipette tip may or may not be removable from a pipette nozzle. In embodiments, a fluid handling system may use a pipette mated with a pipette tip; a pipette tip may be disposable. A tip may form a fluid-tight seal when mated with a pipette. A pipette tip may be used once, twice, or more times. In embodiments, a fluid handling system may use a pipette or similar device, with or without a pipette tip, to aspirate, dispense, mix, transport, or otherwise handle the fluid. The fluid may be dispensed from the fluid handling system when desired. The fluid may be contained within a pipette tip prior to being dispensed, e.g., from an orifice in the pipette tip. In embodiments, or instances during use, all of the fluid may be dispensed; in other embodiments, or instances during use, a portion of the fluid within a tip may be dispensed. A pipette may selectively aspirate a fluid. The pipette may aspirate a selected amount of fluid. The pipette may be capable of actuating stirring mechanisms to mix the fluid within the tip or within a vessel. The pipette may incorporate tips or vessels creating continuous flow loops for mixing, including of materials or reagents that are in non-liquid form. A pipette tip may also facilitate mixture by metered delivery of multiple fluids simultaneously or in sequence, such as in 2-part substrate reactions.

The fluid handling system may include one or more fluidically isolated or hydraulically independent units. For example, the fluid handling system may include one, two, or more pipette tips. The pipette tips may be configured to accept and confine a fluid. The tips may be fluidically isolated from or hydraulically independent of one another. The fluid contained within each tip may be fluidically isolated or hydraulically independent from one fluids in other tips and from other fluids within the device. The fluidically isolated or hydraulically independent units may be movable relative to other portions of the device and/or one another. The fluidically isolated or hydraulically independent units may be individually movable. A fluid handling system may comprise one or more base or support. A base or support may support one or more pipette or pipette units. A base or support may connect one or more pipettes of the fluid handling system to one another.

An automated assay device may be configured to perform processing steps or actions on a sample obtained from a subject. Sample processing may include sample preparation, including, e.g., sample dilution, division of a sample into aliquots, extraction, contact with a reagent, filtration, separation, centrifugation, or other preparatory or processing action or step. An automated assay device may be configured to perform one or more sample preparation action or step on the sample. Optionally, a sample may be prepared for a chemical reaction and/or physical processing step. A sample preparation action or step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads, processing with nanoparticles, or other sample preparation action or steps. For example, sample preparation may include one or more step to separate blood into serum and/or particulate fractions, or to separate any other sample into various components. Sample preparation may include one or more step to dilute and/or concentrate a sample, such as a blood sample, or other biological samples. Sample preparation may include adding an anti-coagulant or other ingredients to a sample. Sample preparation may also include purification of a sample. In embodiments, all sample processing, preparation, or assay actions or steps are performed by a single device. In embodiments, all sample processing, preparation, or assay actions or steps are performed within a housing of a single device. In embodiments, most sample processing, preparation, or assay actions or steps are performed by a single device, and may be performed within a housing of a single device. In embodiments, many sample processing, preparation, or assay actions or steps are performed by a single device, and may be performed within a housing of a single device. In embodiments, sample processing, preparation, or assay actions or steps may be performed by more than one device.

An automated assay device may be configured to run one or more assay on a sample, and to obtain data from the sample. An assay may include one or more physical or chemical treatments, and may include running one or more chemical or physical reactions. An automated assay device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. In embodiments, the volume of a sample may be a small volume, where a small volume may be a volume that is less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. In embodiments, all sample assay actions or steps are performed on a single sample. In embodiments, all sample assay actions or steps are performed by a single device. In embodiments, all sample assay actions or steps are performed within a housing of a single device. In embodiments, most sample assay actions or steps are performed by a single device, and may be performed within a housing of a single device. In embodiments, many sample assay actions or steps are performed by a single device, and may be performed within a housing of a single device. In embodiments, sample processing, preparation, or assay actions or steps may be performed by more than one device.

An automated assay device may be configured to perform a plurality of assays on a sample. In embodiments, an automated assay device may be configured to perform a plurality of assays on a single sample. In embodiments, an automated assay device may be configured to perform a plurality of assays on a single sample, where the sample is a small sample. For example, a small sample may have a sample volume that is a small volume of less than about 1000 µL, or less than about 500 µL, or less than about 250 µL, or less than about 150 µL, or less than about 100 µL, or less than about 75 µL, or less than about 50 µL, or less than about 40 µL, or less than about 20 µL, or less than about 10 µL, or other small volume. An automated assay device may be capable of performing multiplexed assays on a single sample. A plurality of assays may be run simultaneously; may be run sequentially; or some assays may be run simultaneously while others are run sequentially. One or more control assays and/or calibrators (e.g., including a configuration with a control of a calibrator for the assay/tests) can also be incorporated into the device; control assays and assay on calibrators may be performed simultaneously with assays performed on a sample, or may be performed before or after assays performed on a sample, or any combination thereof. In embodiments, all sample assay actions or steps are performed by a single device. In embodiments, all of a plurality of assay actions or steps are performed within a housing of a single device. In embodiments, most sample assay actions or steps, of a plurality of assays, are performed by a single device, and may be performed within a housing of a single device. In embodiments, many sample assay actions or steps, of a plurality of assays, are performed by a single device, and may be performed within a housing of a single device. In embodiments, sample processing, preparation, or assay actions or steps may be performed by more than one device.

In embodiments, all of a plurality of assays may be performed in a short time period. In embodiments, such a short time period comprises less than about three hours, or less than about two hours, or less than about one hour, or less than about 40 minutes, or less than about 30 minutes, or less than about 25 minutes, or less than about 20 minutes, or less than about 15 minutes, or less than about 10 minutes, or less than about 5 minutes, or less than about 4 minutes, or less than about 3 minutes, or less than about 2 minutes, or less than about 1 minute, or other short time period.

An automated assay device may perform nucleic acid assays, including isothermal nucleic acid assays (e.g., assays for detecting and measuring nucleic acid targets in a sample, including DNA and RNA targets). In embodiments, an automated assay device may perform nucleic acid assays as disclosed in U.S. patent application Ser. No. 14/183,503, filed Feb. 18, 2014; U.S. patent application Ser. No. 14/214, 850, filed Mar. 15, 2014; International Patent Application PCT/US2014/030034, filed Mar. 15, 2014; and in International Patent Application PCT/US2014/056151, filed Sep. 17, 2014. An automated assay device may perform antibody assays, including enzyme-linked immunosorbent assays (ELISA), and other assays for detecting and measuring the amounts of proteins (including antibodies), peptides, and small molecules in samples. An automated assay device may perform general chemistry assays, including electrolyte assays (e.g., assays for detecting and measuring the amounts of electrolytes such as sodium and potassium in a sample).

An automated assay device may be configured to detect one or more signals relating to the sample. An automated assay device may be configured to identify one or more properties of the sample. For instance, the automated assay device may be configured to detect the presence or concentration of one analyte or a plurality of analytes or a disease condition in the sample (e.g., in or through a bodily fluid, secretion, tissue, or other sample). Alternatively, the automated assay device may be configured to detect a signal or signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A chemical reaction or other processing step may be performed, with or without the sample. Examples of steps, tests, or assays that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation action or steps, or combinations thereof. Steps, tests, or assays that may be prepared or run by the device may include imaging, including microscopy, cytometry, and other techniques preparing or utilizing images. Steps, tests, or assays that may be prepared or run by the device may further include an assessment of histology, morphology, kinematics, dynamics, and/or state of a sample, which may include such assessment for cells.

A device may be capable of performing all on-board steps (e.g., steps or actions performed by a single device) in a short amount of time. A device may be capable of performing all on-board steps on a single sample in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less. The amount of time from accepting a sample within the device to transmitting data and/or to analysis from the device regarding such a sample may depend on the type or number of steps, tests, or assays performed on the sample. The amount of time from accepting a sample within the device to transmitting data and/or to analysis from the device regarding such a sample may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, or 1 minute or less.

A device may be configured to prepare a sample for disposal, or to dispose of a sample, such as a biological sample, following processing or assaying of a sample.

In embodiments, an automated assay device may be configured to transmit data obtained from a sample. In embodiments, an automated assay device may be configured to communicate over a network. An automated assay device may include a communication module that may interface with the network. An automated assay device may be connected to the network via a wired connection or wirelessly. The network may be a local area network (LAN) or a wide area network (WAN) such as the Internet. In some embodiments, the network may be a personal area network. The network may include the cloud. The automated assay device may be connected to the network without requiring an intermediary device, or an intermediary device may be required to connect an automated assay device to a network. An automated assay device may communicate over a network with another device, which may be any type of networked device, including but not limited to a personal computer, server computer, or laptop computer; personal digital assistants (PDAs) such as a Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Such communication may include providing data to a cloud computing infrastructure or any other type of data storage infrastructure which may be accessed by other devices.

An automated assay device may provide data regarding a sample to, e.g., a health care professional, a health care professional location, such as a laboratory, or an affiliate thereof. One or more of a laboratory, health care professional, or subject may have a network device able to receive or access data provided by the automated assay device. An automated assay device may be configured to provide data regarding a sample to a database. An automated assay device may be configured to provide data regarding a sample to an electronic medical records system, to a laboratory information system, to a laboratory automation system, or other system or software. An automated assay device may provide data in the form of a report.

A laboratory, device, or other entity or software may perform analysis on data regarding a sample in real-time. A software system may perform chemical analysis and/or pathological analysis, or these could be distributed amongst combinations of lab, clinical, and specialty or expert personnel. Analysis may include qualitative and/or quantitative evaluation of a sample. Data analysis may include a subsequent qualitative and/or quantitative evaluation of a sample. Optionally, a report may be generated based on raw data, pre-processed data, or analyzed data. Such a report may be prepared so as to maintain confidentiality of the data obtained from the sample, the identity and other information regarding the subject from whom a sample was obtained, analysis of the data, and other confidential information. The report and/or the data may be transmitted to a health care professional. Data obtained by an automated assay device, or analysis of such data, or reports, may be provided to a database, an electronic medical records system, to a laboratory information system (LIS), to a laboratory automation system (LAS), or other system or software.

Description and disclosure of examples of reagents, assays, methods, kits, devices, and systems which may use, or be used with, the methods, devices, and systems disclosed herein may be found, for example, in U.S. Pat. No. 8,088,593; 8,380,541; 8,435,738; 8,475,739; 8,840,838; U.S. patent application Ser. No. 14/183,503, filed Feb. 18, 2014; U.S. patent application Ser. No. 13/933,035, filed Jul. 1, 2013; U.S. patent application Ser. No. 13/769,820, filed Feb. 18, 2013; U.S. patent application Ser. No. 14/183,503, filed Feb. 18, 2014; patent application Ser. No. 14/214,850, filed Mar. 15, 2014; International Patent Application PCT/US2014/030034, filed Mar. 15, 2014; International Patent Application PCT/US2014/056151, filed Sep. 17, 2014; U.S. patent application Ser. No. 13/769,798, filed Feb. 18, 2013; U.S. patent application Ser. No. 13/769,779, filed Feb. 18, 2013; U.S. patent application Ser. No. 13/244,947 filed Sep. 26, 2011; PCT/US2012/57155, filed Sep. 25, 2012; U.S. application Ser. No. 13/244,946, filed Sep. 26, 2011; U.S. patent application Ser. No. 13/244,949, filed Sep. 26, 2011; and U.S. application Ser. No. 13/945,202, filed Jul. 18, 2013, the disclosures of which patents and patent applications are all hereby incorporated by reference in their entireties.

Description and Use of Transfer Vessels and Holding Vessels

A fingerstick blood sample may be collected from a subject by puncturing the skin of an extremity of the subject (e.g., by applying a lancet) and collecting capillary blood that flows from the resulting wound in a holding vessel. Such a blood sample is typically a small volume blood sample. Larger volumes of blood may be collected by collecting such fingerstick blood into a holding vessel having two or more holding chambers (cavities), or multiple holding vessels, and may be collected from two or more fingerstick wounds. A holding vessel may include sample separation gel. A sample preparation gel may include, for example polysaccharide (e.g., Ficoll), poly dimethyl siloxane (e.g., poly dimethyl siloxane polymers), or other materials or material combinations which aid in the separation of blood contents. Centrifugation of a blood sample in a holding vessel having a sample preparation gel (termed "gel" hereafter) may separate the blood sample into fractions, i.e., a fraction above the gel and a fraction below the gel (where below refers to the portion of the holding vessel subject to the greatest centrifugal force during centrifugation). Such centrifugation is typically effective to separate a blood sample into a cell-containing layer below the gel, and a plasma layer above the gel. Centrifugation for separating a blood sample into fractions in this way may be, for example, centrifugation at about 500×g to about 5000×g; or at about 750×g to about 4000×g; or at about 900×g to about 3000×g; or at about 1000×g to about 2500×g; or other amount of centrifugation. In embodiments, such centrifugation may be applied for about 1 to about 60 minutes, or for about 2 to about 30 minutes, or for about 3 to about 20 minutes, or for about 5 to 15 minutes.

In embodiments, following this centrifugation, the holding vessel may be stored (e.g., may be stored in a refrigerated container or space). In embodiments, following this centrifugation, the holding vessel may be transported to another location; the holding vessel may be stored at the other location. In embodiments, the holding vessel may be stored at the same location (e.g., the location at which the sample was collected).

Typically, the sample held in the holding vessel must be removed from the holding vessel for analysis of the sample. In many instances, the upper (plasma) fraction of a blood sample is analyzed separately from the cell-containing fraction. However, complete removal of the upper (plasma) fraction may include removal of some gel along with the plasma, or may include removal of some cells along with the plasma, or may include removal of both gel and cells along with the plasma. In order to avoid contamination of a plasma sample by gel or cells, or both, some plasma may be left in the holding vessel (such remaining sample is termed "overage"). For example, removal of a plasma sample from a small volume holding vessel (e.g., a holding vessel with an internal volume (cavity) of about 100 µL) and having a gel may leave about 20 µL or more of plasma (overage). However, it is undesirable to leave some plasma sample in the holding vessel, particularly where the sample is a small volume sample. Accordingly, improved procedures for removing sample from holding vessels which reduce the amount of sample left in the holding vessel provide useful improvements over procedures which waste sample by leaving undesirable amounts in the holding vessel.

Use of a transfer vessel as disclosed herein allows for plasma recovery from the sample collection device with minimal overage. This is achieved by transferring plasma sample from two or more small volume, gel-containing holding vessels by gentle centrifugation into a transfer vessel as disclosed herein. The resulting combined sample may be aspirated as needed for sample analysis (e.g., by an automated sample analysis device or system) with minimal overage.

In embodiments, a holding vessel is placed with its open mouth positioned over the open mouth of a transfer vessel. In embodiments, two holding vessels are placed with their open mouths positioned over the open mouth of a transfer vessel. In embodiments, a plurality of holding vessels are placed with their open mouths positioned over the open mouth of a transfer vessel. Such placement may allow free flow of the plasma sample from the holding vessel(s) into the transfer vessel. In embodiments, the flow of plasma sample from the holding vessel(s) into the transfer vessel is aided by application of gentle centrifugation.

In embodiments, such gentle centrifugation of a holding vessel, or of two or more holding vessels, placed with their open mouths positioned over the open mouth of a transfer vessel may be, for example, centrifugation at about 0.25×g to about 100×g; or at about 0.5×g to about 50×g; or at about 0.75×g to about 25×g; or at about 1×g to about 10×g; or other amount of centrifugation. In embodiments, such gentle centrifugation may be applied for about 20 seconds to about 10 minutes, or for about 30 seconds to about 5 minutes, or for about 45 seconds to about 3 minutes, or for about 1 minute. In embodiments, such gentle centrifugation may be centrifugation at about 10×g for about 1 minute.

In embodiments, two or more holding vessels are placed in a rack with their open mouths positioned over the open mouth of a transfer vessel, and centrifuged at about 10×g for about 1 minute. In embodiments, 10 or more holding vessels are placed in a rack with their open mouths positioned over the open mouth of a transfer vessel, and centrifuged at about 10×g for about 1 minute. In embodiments, 20 or more holding vessels are placed in a rack with their open mouths positioned over the open mouth of a transfer vessel, and centrifuged at about 10×g for about 1 minute. In embodiments, about 25 holding vessels are placed in a rack with their open mouths positioned over the open mouth of a transfer vessel, and centrifuged at about 10×g for about 1 minute.

Following such gentle centrifugation, plasma may be removed from the transfer vessel, e.g., for analysis. In embodiments, such removal may be within an automatic sample analysis device or system.

Figure 1B:
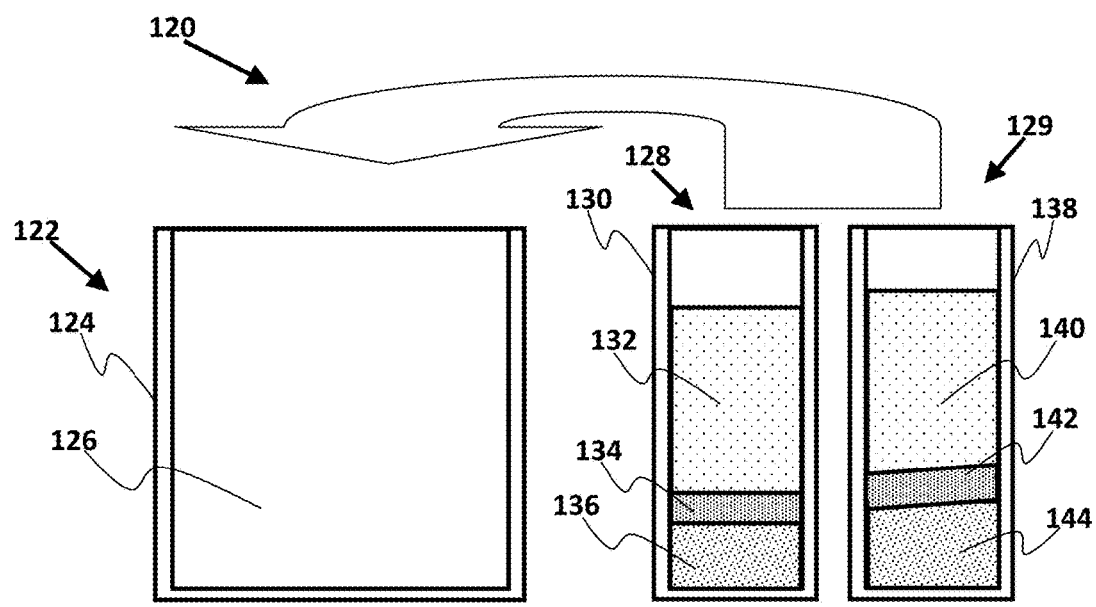
FIG. 1B shows a transfer vessel and two holding vessels, with fluid samples in both of the holding vessels. The large arrow indicates the transfer of at least a portion or fraction of the sample from both of the holding vessels to the transfer vessel. The sample (or portions or fractions thereof) from both holding vessels is combined within the cavity of the transfer vessel.

A transfer vessel may have a shape as illustrated in FIGS. 1A and 1B, and may have a receptacle having an internal volume of at least about 60 µL; thus, at least about 60 µL of fluid may be transferred from the sample vessel to the transfer vessel. Such transfer may be performed, for example, by pouring a fluid sample from the sample vessel (which originally held the fluid sample) into the transfer vessel; or may be performed by pipetting a fluid sample from the sample vessel (which originally held the fluid sample) and then pipetting the fluid sample into the transfer vessel; or by other means of transfer.

A transfer vessel system be labeled. For example, a transfer vessel may have a bar code, a QR code, a serial number, a tag, or other identifying sign, mark, or attachment. For example, a transfer vessel may include a label which provides means to associate a sample held by the transfer vessel with the patient from which the sample was obtained; such association may be provided, e.g., by means of a QR code.

A transfer vessel system (i.e., including at least a transfer vessel and a sample vessel) may be labeled. For example, a transfer vessel and a sample vessel may each have a bar code, a QR code, a serial number, a tag, or other identifying sign, mark, or attachment, where the sample vessel label includes identifying information useful to identify the sample vessel and its corresponding transfer vessel, and where the transfer vessel label includes identifying information useful to identify the transfer vessel and its corresponding sample vessel. For example, a label may include information which provides means to associate a sample originally held in a sample vessel and which is held by the transfer vessel following transfer with the patient from which the sample was obtained; such association may be provided, e.g., by means of a QR code.

FIG. 1A shows a system 100 including a transfer vessel 104 having a transfer vessel interior cavity 106, and a holding vessel 110 holding a fluid sample, including plasma fraction 112, gel 114, and cell-containing fraction 116 in the holding vessel 110. The large arrow indicates the transfer of at least a portion or fraction of the sample from the holding vessel 110 to the transfer vessel 104.

FIG. 1B shows a system 120 including a transfer vessel 124 and two holding vessels 130 and 138, with fluid samples in both of the holding vessels. Holding vessel 130 holds a fluid sample, including plasma fraction 132, gel 134, and cell-containing fraction 136; holding vessel 138 holds a fluid sample, including plasma fraction 140, gel 142, and cell-containing fraction 144. Note that the volume of sample in holding vessel 130 is different than the volume of sample held in holding vessel 138. In addition, the gel in holding vessel 138 is at a different height within the that holding vessel than is the gel in holding vessel 130; the gel in holding vessel 138 is also disposed at an angle to the walls of holding vessel 138. The large arrow indicates the transfer of at least a portion or fraction of the sample from both of the holding vessels to the transfer vessel 122. Following transfer, the sample (or portions or fractions thereof) from both holding vessels is combined within the cavity of the transfer vessel.

Figure 1C:
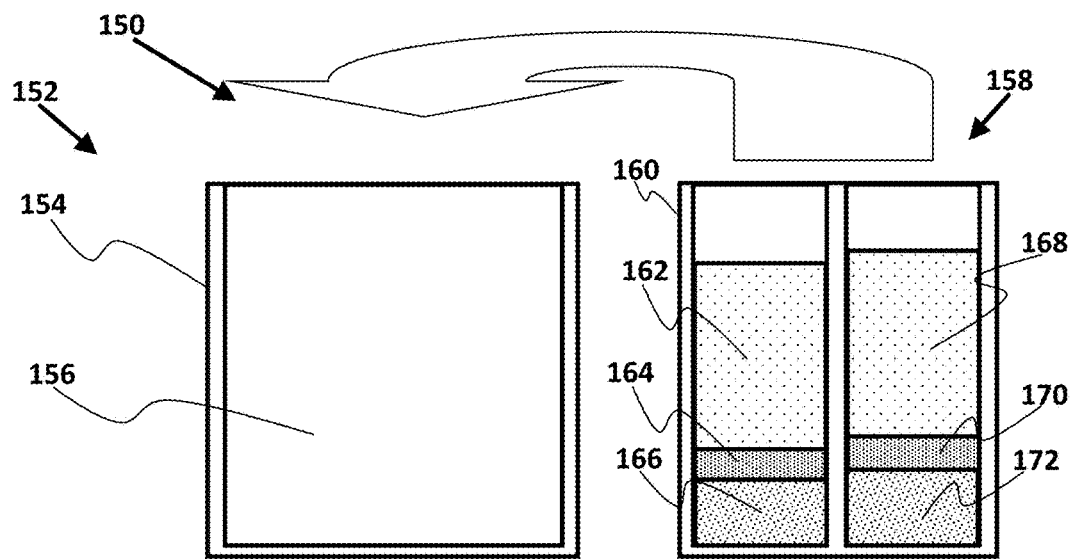
FIG. 1C shows a transfer vessel and a holding vessel having two compartments, with fluid samples in both of the compartments. The large arrow indicates the transfer of at least a portion or fraction of the sample from both of the holding vessel compartments to the transfer vessel. The sample (or portions or fractions thereof) from both compartments is combined within the cavity of the transfer vessel.

FIG. 1C shows a system 150 including a transfer vessel 154 with an interior cavity 156, and a holding vessel 160 having two compartments, with fluid samples in both of the compartments. Holding vessel 150 holds a fluid sample on its left side as shown in the figure, including plasma fraction 162, gel 164, and cell-containing fraction 166; holding vessel 150 also holds a fluid sample on its right side as shown in the figure, including plasma fraction 168, gel 170, and cell-containing fraction 172. The large arrow indicates the transfer of at least a portion or fraction of the sample from both of the holding vessel compartments to the transfer vessel. Following this transfer, the sample (or portions or fractions thereof) from both compartments is combined within the cavity of the transfer vessel.

Figure 1D:
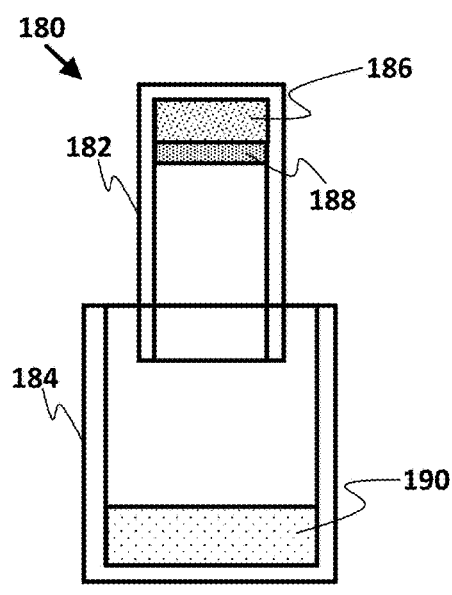
FIG. 1D shows a first exemplary configuration for providing sample from a holding vessel to a transfer vessel.

FIG. 1D shows a first exemplary configuration for providing sample from a holding vessel 182 to a transfer vessel 184. System 180 includes a transfer vessel 184 and a holding vessel 182. Plasma sample 190 is held within transfer vessel 184 while gel 188 and cell-containing fraction 186 remains in holding vessel 182.

Figure 1E:
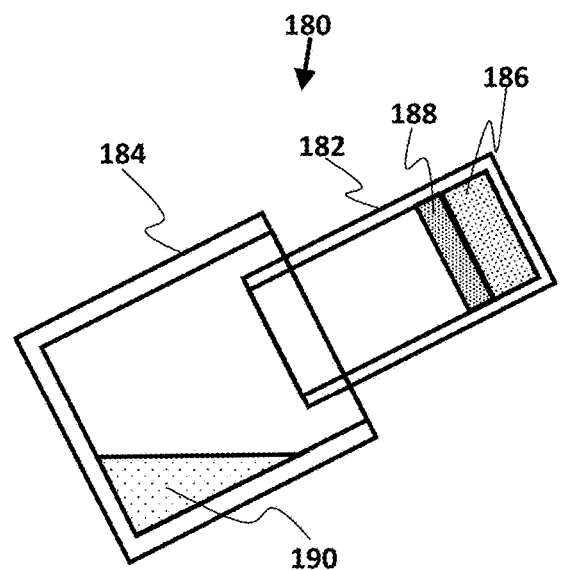
FIG. 1E shows a second exemplary configuration for providing sample from a holding vessel to a transfer vessel.

FIG. 1E shows a second exemplary configuration for providing sample from a holding vessel 182 to a transfer vessel 184. System 180 includes a transfer vessel 184 and a holding vessel 182. Plasma sample 190 is held within transfer vessel 184 while gel 188 and cell-containing fraction 186 remains in holding vessel 182.

Figure 2A:
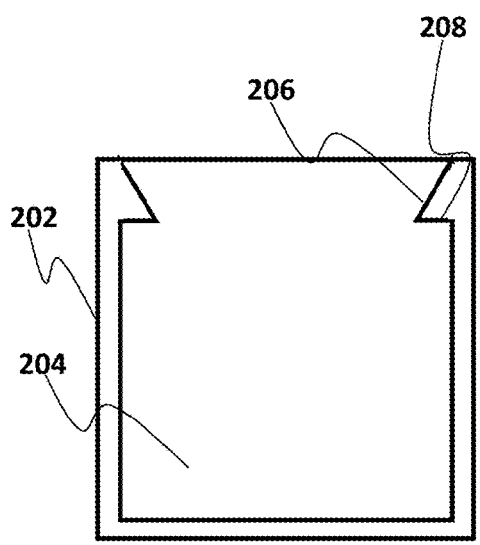
FIG. 2A shows a cross-sectional view of a transfer vessel having features as disclosed herein. In embodiments, a transfer vessel as illustrated in the figure may have a three-dimensional shape that is cylindrical, or rectangular, square, or pyramidal, or other shape having a cross-section as shown.

FIG. 2A shows a cross-sectional view of a transfer vessel 202 having features as disclosed herein. A transfer vessel 202 may have an interior bevel 206, which may have a lower interior wall 208. An interior bevel 206 may be useful to guide, and may be useful to hold, a holding vessel disposed over (or in) the open mouth of a transfer vessel 202 for transfer of sample from the holding vessel to a transfer vessel 202. In embodiments, a transfer vessel 202 as illustrated in the figure may have a three-dimensional shape that is cylindrical, or rectangular, square, or pyramidal, or other shape having a cross-section as shown.

Figure 2B:
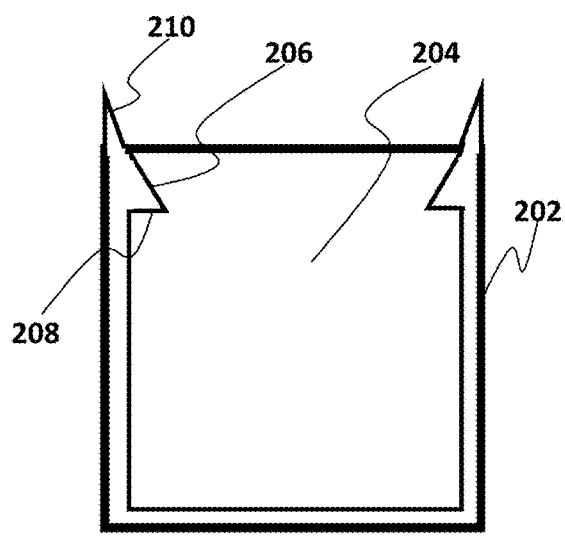
FIG. 2B shows a cross-sectional view of a transfer vessel having features as disclosed herein. In embodiments, a transfer vessel as illustrated in the figure may have a three-dimensional shape that is cylindrical, or rectangular, square, or pyramidal, or other shape having a cross-section as shown.

FIG. 2B shows a cross-sectional view of a transfer vessel having features as disclosed herein. A transfer vessel 202 may have an interior bevel 206, which may have a lower interior wall or shoulder 208, and may include at least a portion 210 which extends outwardly from the interior of the transfer vessel 202. An interior bevel 206 and an outer bevel 210 may be useful to guide, and may be useful to hold, a holding vessel disposed over (or in) the open mouth of a transfer vessel 202 for transfer of sample from the holding vessel to a transfer vessel 202. In embodiments, a transfer vessel as illustrated in the figure may have a three-dimensional shape that is cylindrical, or rectangular, square, or pyramidal, or other shape having a cross-section as shown.

Figure 2C:
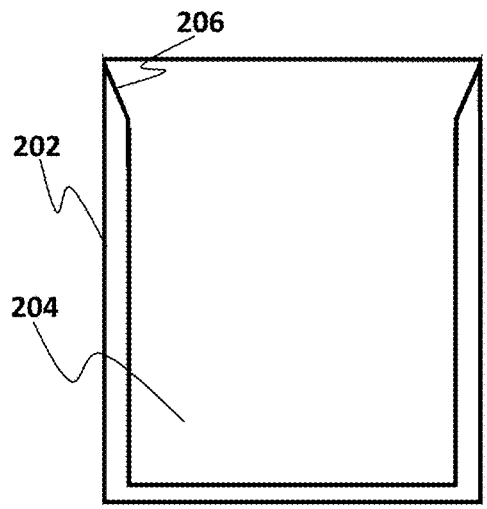
FIG. 2C shows a cross-sectional view of a transfer vessel having features as disclosed herein. In embodiments, a transfer vessel as illustrated in the figure may have a three-dimensional shape that is cylindrical, or rectangular, square, or pyramidal, or other shape having a cross-section as shown.

FIG. 2C shows a cross-sectional view of a transfer vessel having features as disclosed herein. A transfer vessel 202 may have an interior bevel 206. An interior bevel 206 may be useful to guide, and may be useful to hold, a holding vessel disposed over (or in) the open mouth of a transfer vessel 202 for transfer of sample from the holding vessel to a transfer vessel 202. In embodiments, a transfer vessel as illustrated in the figure may have a three-dimensional shape that is cylindrical, or rectangular, square, or pyramidal, or other shape having a cross-section as shown.

Figure 2D:
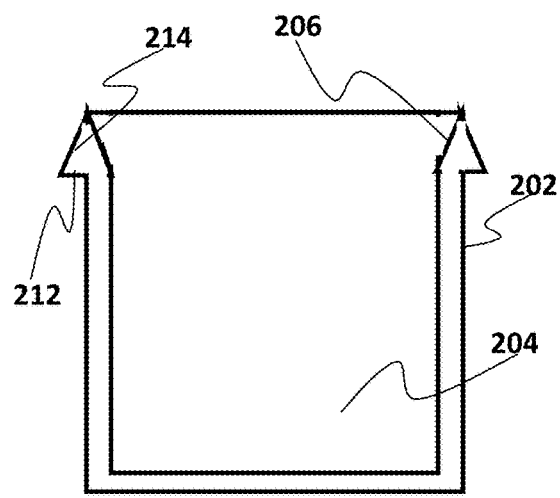
FIG. 2D shows a cross-sectional view of a transfer vessel having features as disclosed herein. In embodiments, a transfer vessel as illustrated in the figure may have a three-dimensional shape that is cylindrical, or rectangular, square, or pyramidal, or other shape having a cross-section as shown.

FIG. 2D shows a cross-sectional view of a transfer vessel having features as disclosed herein. A transfer vessel 202 may have an interior bevel 206, which may have an outer bevel 214 and may have a lower outer wall 212. An interior bevel 206 may be useful to guide, and may be useful to hold, a holding vessel disposed over (or in) the open mouth of a transfer vessel 202 for transfer of sample from the holding vessel to a transfer vessel 202. In embodiments, a transfer vessel as illustrated in the figure may have a three-dimensional shape that is cylindrical, or rectangular, square, or pyramidal, or other shape having a cross-section as shown.

In embodiments, a transfer vessel may include a tab, a flange, a slot, a notch, or other feature which may be useful in holding, attaching, guiding, or otherwise directing a holding vessel into position for transfer of sample to a transfer vessel. In embodiments, a transfer vessel may include a tab, a flange, a slot, a notch, or other feature which may be useful in holding, attaching, guiding, or otherwise placing or securing a transfer vessel in or into position for transfer of sample from a holding vessel to a transfer vessel.

Figure 3A:
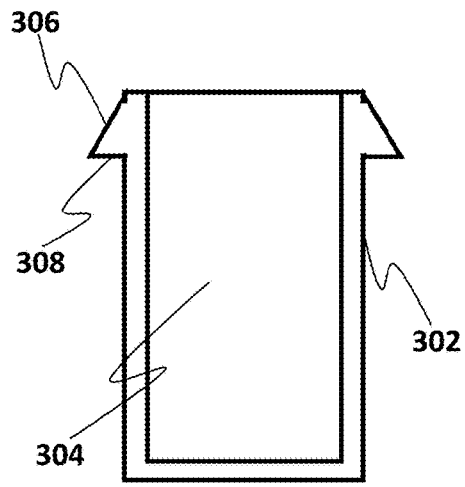
FIG. 3A shows a cross-sectional view of a holding vessel having features as disclosed herein. In embodiments, a holding vessel as illustrated in the figure may have a three-dimensional shape that is cylindrical, or rectangular, square, or pyramidal, or other shape having a cross-section as shown.

FIG. 3A shows a cross-sectional view of a holding vessel having features as disclosed herein. A holding vessel 302 may have an interior cavity 304, and an external bevel 306, which may have a lower wall 308. An interior bevel 306 may be useful to guide, and may be useful to hold, a holding vessel disposed over (or in) the open mouth of a transfer vessel for transfer of sample from the holding vessel to a transfer vessel. In embodiments, a holding vessel as illustrated in the figure may have a three-dimensional shape that is cylindrical, or rectangular, square, or pyramidal, or other shape having a cross-section as shown.

Figure 3B:
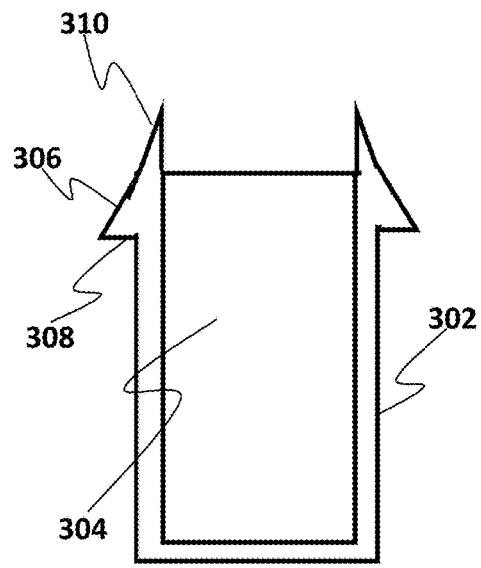
FIG. 3B shows a cross-sectional view of a holding vessel having features as disclosed herein. In embodiments, a holding vessel as illustrated in the figure may have a three-dimensional shape that is cylindrical, or rectangular, square, or pyramidal, or other shape having a cross-section as shown.

FIG. 3B shows a cross-sectional view of a holding vessel having features as disclosed herein. A holding vessel 302 may have an interior cavity 304, and an external bevel 306, which may have a lower wall or shoulder 308 and may include a portion 310 which extends outwardly. An interior bevel 306 may be useful to guide, and may be useful to hold, a holding vessel disposed over (or in) the open mouth of a transfer vessel for transfer of sample from the holding vessel to a transfer vessel. In embodiments, a holding vessel as illustrated in the figure may have a three-dimensional shape that is cylindrical, or rectangular, square, or pyramidal, or other shape having a cross-section as shown.

Figure 3C:
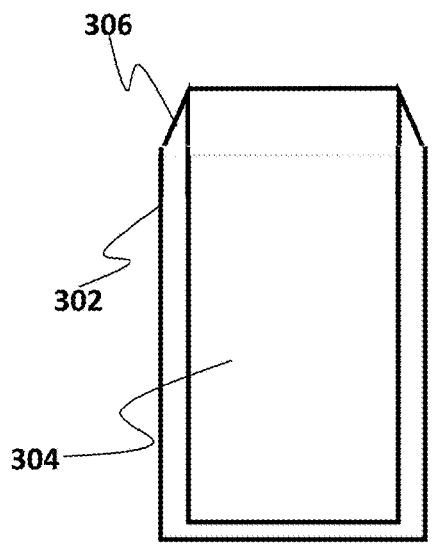
FIG. 3C shows a cross-sectional view of a holding vessel having features as disclosed herein. In embodiments, a holding vessel as illustrated in the figure may have a three-dimensional shape that is cylindrical, or rectangular, square, or pyramidal, or other shape having a cross-section as shown.

FIG. 3C shows a cross-sectional view of a holding vessel having features as disclosed herein. A holding vessel 302 may have an interior cavity 304, and an external bevel 306. An interior bevel 306 may be useful to guide, and may be useful to hold, a holding vessel disposed over (or in) the open mouth of a transfer vessel for transfer of sample from the holding vessel to a transfer vessel. In embodiments, a holding vessel as illustrated in the figure may have a three-dimensional shape that is cylindrical, or rectangular, square, or pyramidal, or other shape having a cross-section as shown.

Figure 3D:
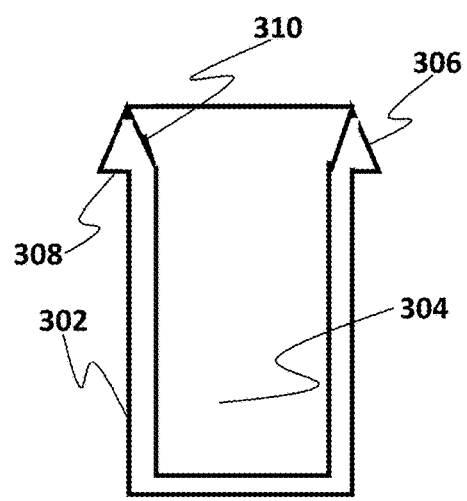
FIG. 3D shows a cross-sectional view of a holding vessel having features as disclosed herein. In embodiments, a holding vessel as illustrated in the figure may have a three-dimensional shape that is cylindrical, or rectangular, square, or pyramidal, or other shape having a cross-section as shown.

FIG. 3D shows a cross-sectional view of a holding vessel having features as disclosed herein. A holding vessel 302 may have an interior cavity 304, and an external bevel 306, which may have a lower wall 308 and an internal bevel 310. An interior bevel 306 may be useful to guide, and may be useful to hold, a holding vessel disposed over (or in) the open mouth of a transfer vessel for transfer of sample from the holding vessel to a transfer vessel. In embodiments, a holding vessel as illustrated in the figure may have a three-dimensional shape that is cylindrical, or rectangular, square, or pyramidal, or other shape having a cross-section as shown.

In embodiments, a holding vessel may include a tab, a flange, a slot, a notch, or other feature which may be useful in holding, attaching, guiding, or otherwise directing a holding vessel into position for transfer of sample to a transfer vessel.

Figure 4A:
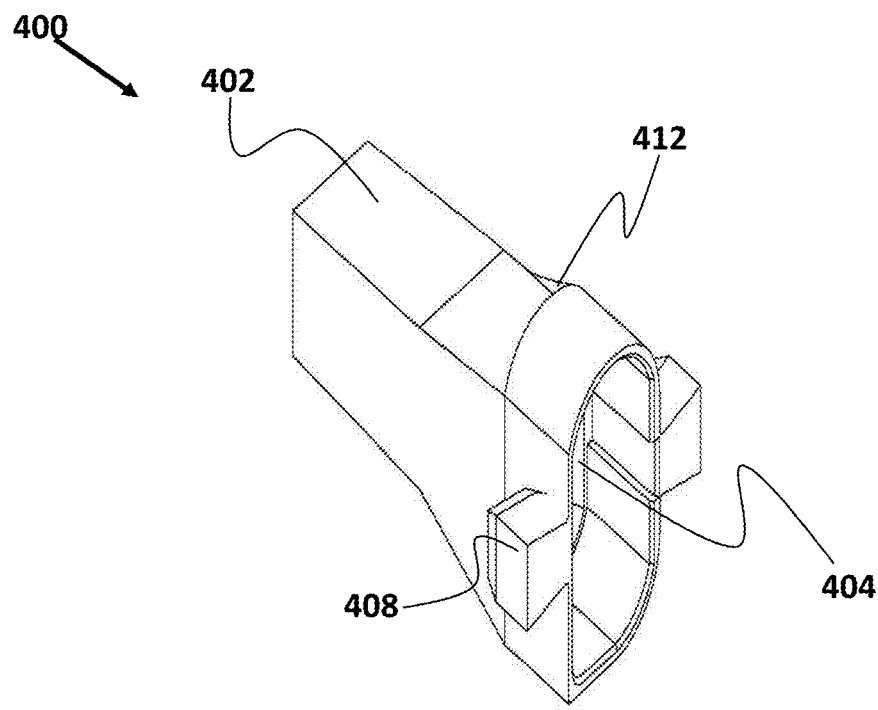
FIG. 4A shows a perspective view of a transfer vessel having features as disclosed herein.

FIG. 4A shows a perspective view of a transfer vessel having features as disclosed herein. Transfer vessel 402 has an opening 404 leading to the internal cavity of the transfer vessel 402, and has a flange 408. A rim 412 is also shown.

Figure 4B:
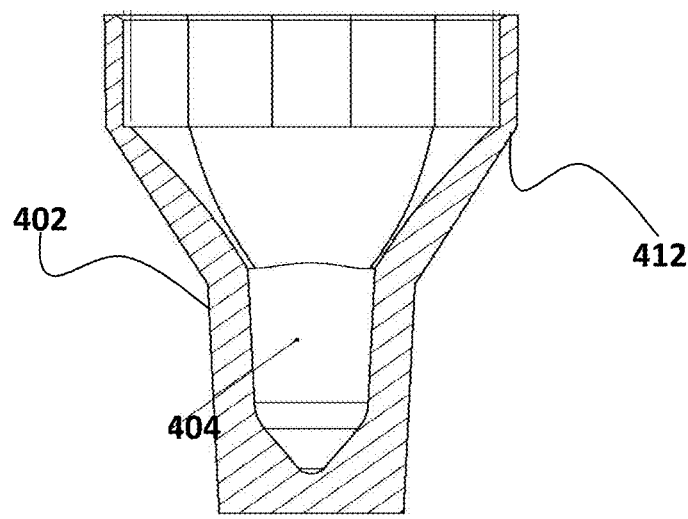
FIG. 4B shows a cross-sectional view of a transfer vessel having features as disclosed herein.

FIG. 4B shows a cross-sectional view of a transfer vessel as shown in FIG. 4A having features as disclosed herein.

Figure 5:
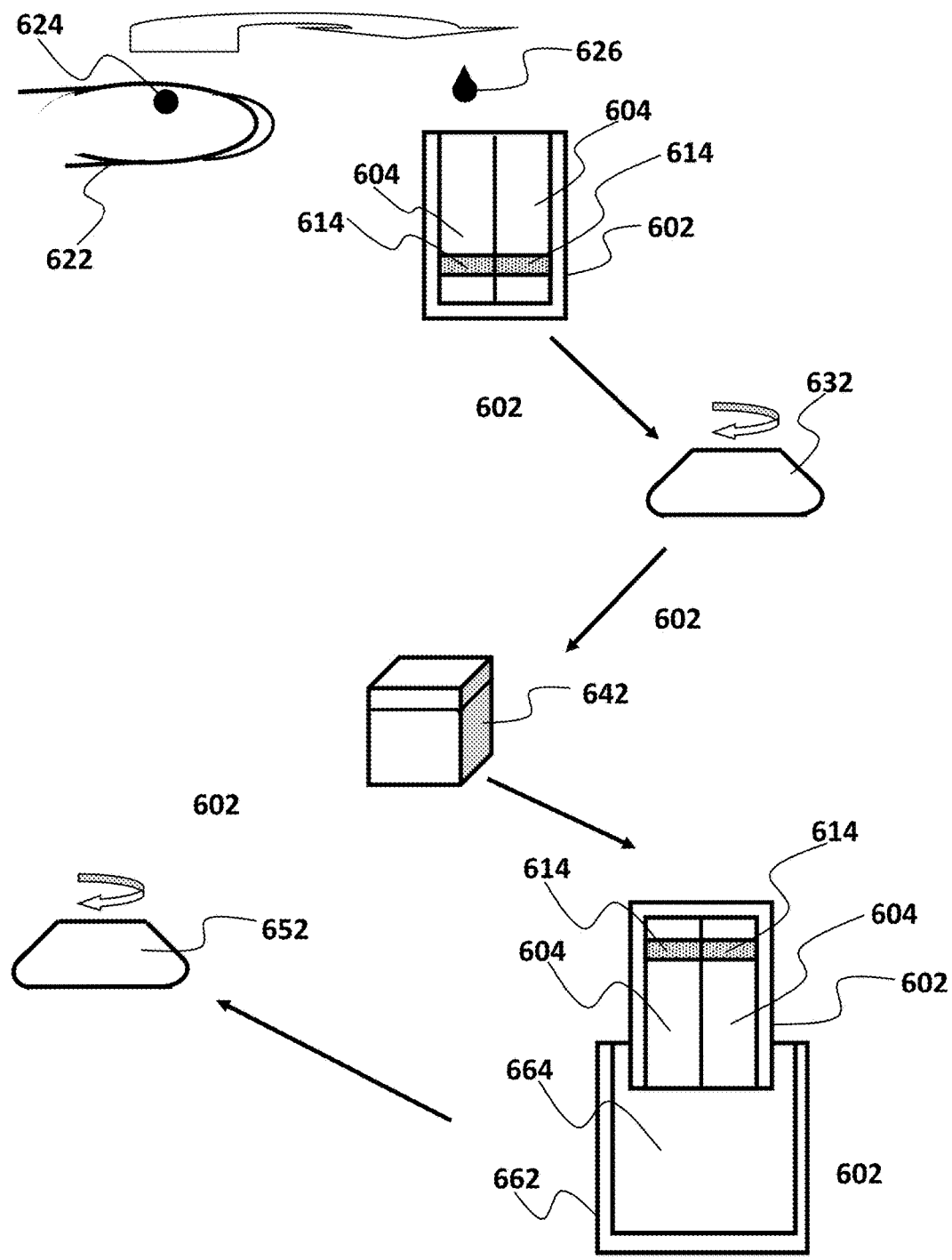
FIG. 5 shows a schematic illustration of a method of obtaining fingerstick blood samples and providing the samples to a transfer vessel as disclosed herein.

FIG. 5 shows a schematic illustration of a method of obtaining fingerstick blood samples and providing the samples to a transfer vessel as disclosed herein. A finger 22 has a wound 624 from which blood is emerging. A small volume 626 of that blood is placed in a holding vessel 602 which has two compartments, with upper portions 604 and gel 614. Blood is placed in both compartments. The holding vessel 602 with its blood samples in both compartments is centrifuged at high speed (e.g., at about 500×g to about 5000×g; or at about 750×g to about 4000×g; or at about 900×g to about 3000×g; or at about 1000×g to about 2500×g; for about 1 to about 60 minutes, or for about 2 to about 30 minutes, or for about 3 to about 20 minutes, or for about 5 to 15 minutes). Following this centrifugation, the holding vessel may be placed in a rack or box, for storage, transport, or both. The holding vessel, and in embodiments, including rack or box, maybe refrigerated (e.g., stored at low temperature, such as 4° C. or other low temperature) prior to or during storage or transport.

Following such placement, and prior to analysis of the sample, the holding vessel, which may still be held in a rack (e.g., with other holding vessels) is positioned with the open mouths of both compartments over the open mouth of transfer vessel 602. The holding vessel and the transfer vessel 662 are gently centrifuged in this configuration, so that the plasma fraction of both sample compartments flow into the transfer vessel 662 without gel or cell-containing fraction flowing into the transfer vessel. Gentle centrifugation may be, for example, centrifugation at about 10×g for about 1 minute. In embodiments, such gentle centrifugation may include centrifugation at about 0.25×g to about 100×g; or at about 0.5×g to about 50×g; or at about 0.75×g to about 25×g; or at about 1×g to about 10×g; or other amount of centrifugation. In embodiments, such gentle centrifugation may be applied for about 20 seconds to about 10 minutes, or for about 30 seconds to about 5 minutes, or for about 45 seconds to about 3 minutes, or for about 1 minute.

Such methods provide uncontaminated plasma fraction samples from fingerstick blood samples with less loss of sample than other methods. Transfer and combination of small volume samples into a single transfer vessel, for use of the combined sample for sample analysis, provides uncontaminated sample with little loss of sample to overage or other wastage.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm/

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are fully incorporated herein by reference for all purposes:

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

COPYRIGHT

This document contains material subject to copyright protection. The copyright owner (the Applicant) has no objection to facsimile reproduction of the patent documents and disclosures, as they appear in the US Patent and Trademark Office patent file or records, but otherwise reserves all copyright rights whatsoever. The following notice shall apply: Copyright 2015 Theranos, Inc.

What is claimed is:

1. A method of providing a small volume fluid sample for analysis, comprising:

placing small volume fluid samples in separate compartments of a holding vessel having at least two compartments, each compartment containing gel and having a compartment mouth;

centrifuging the holding vessel;

placing the holding vessel with each compartment mouth positioned in or near the mouth of a transfer vessel; and applying gentle centrifugation to the holding vessel and transfer vessel, wherein the holding vessel mouths and the transfer vessel mouth remain in position during said gentle centrifugation effective that a fraction of the sample flows from both the compartments of the holding vessel into the transfer vessel.

2. The method of claim 1, wherein said small volume fluid sample is a small volume blood sample.

3. The method of claim 1, wherein said small volume fluid sample is a fingerstick blood sample.

4. The method of claim 1, further comprising analyzing the fluid sample with an automated sample analysis device.

5. The method of claim 1, further comprising analyzing the fluid sample with an automated sample analysis system.

6. A method of providing a small volume fluid sample for analysis, comprising:

placing small volume fluid samples in separate compartments of a holding vessel having at least two compartments, each compartment containing gel and having a compartment mouth;

centrifuging the holding vessel;

placing the holding vessel with each compartment mouth positioned in or near the mouth of a transfer vessel; and applying gentle centrifugation to the holding vessel and transfer vessel, wherein the holding vessel mouths and the transfer vessel mouth remain in position during said gentle centrifugation effective that a fraction of the sample flows from both the compartments of the holding vessel into the transfer vessel;

wherein said gel comprises plasma separation gel.

7. A method of providing a small volume fluid sample for analysis, comprising:

placing small volume fluid samples in separate compartments of a holding vessel having at least two compartments, each compartment containing gel and having a compartment mouth;

centrifuging the holding vessel;

placing the holding vessel with each compartment mouth positioned in or near the mouth of a transfer vessel; and applying gentle centrifugation to the holding vessel and transfer vessel, wherein the holding vessel mouths and the transfer vessel mouth remain in position during said gentle centrifugation effective that a fraction of the sample flows from both the compartments of the holding vessel into the transfer vessel;

wherein said fraction of the sample that flows from both the compartments of the holding vessel into the transfer vessel is a plasma sample.

* * * * *